(12) United States Patent
Ogawa

(10) Patent No.: US 6,890,296 B2
(45) Date of Patent: May 10, 2005

(54) MEASURING ENDOSCOPE APPARATUS

(75) Inventor: Kiyotomi Ogawa, Tokyo (JP)

(73) Assignee: Olympus Corporation (JP)

( * ) Notice: Subject to any disclaimer, the term of this patent is extended or adjusted under 35 U.S.C. 154(b) by 244 days.

(21) Appl. No.: 10/158,235

(22) Filed: May 29, 2002

(65) Prior Publication Data

US 2002/0183590 A1 Dec. 5, 2002

(30) Foreign Application Priority Data

May 30, 2001 (JP) ......................................... 2001-162869

(51) Int. Cl.$^7$ ................................................. A61B 1/04
(52) U.S. Cl. ...................................... 600/118; 600/175
(58) Field of Search ................................. 600/103, 109, 600/117, 118, 175, 172, 181; 348/75, 76, 65

(56) References Cited

U.S. PATENT DOCUMENTS

| | | | | |
|---|---|---|---|---|
| 5,860,912 A | * | 1/1999 | Chiba | .......................... 600/111 |
| 6,063,023 A | | 5/2000 | Sakiyama et al. | ........... 600/118 |
| 6,517,478 B2 | * | 2/2003 | Khadem | ..................... 600/117 |
| 6,556,237 B1 | * | 4/2003 | Fredlund et al. | ............... 348/96 |
| 2002/0161284 A1 | * | 10/2002 | Tanaka | ........................ 600/176 |

FOREIGN PATENT DOCUMENTS

| | | |
|---|---|---|
| JP | 10-248806 | 9/1998 |
| JP | 2001-275934 | 10/2001 |

* cited by examiner

Primary Examiner—John P. Leubecker
(74) Attorney, Agent, or Firm—Ostrolenk, Faber, Gerb & Soffen, LLP

(57) ABSTRACT

A processing unit includes a positional relationship information extracting unit for extracting first information on a positional relationship of an optical adaptor by performing the image processing of a signal transmitted from an image pick-up unit upon capturing the image of a predetermined subject, a storing device for storing the first information on the positional relationship, a comparing and determining unit for comparing the first information on the positional relationship stored in the storing device with second information on the positional relationship which is extracted again by the extracting unit when replacing the optical adaptor by using the tip of an endoscope insertion portion, and a notifying unit for notifying a determination result based on determination information from the comparing and determining unit. Thus, it is possible to prevent the execution of measuring from deteriorating the precision by the change in positional relationship between an optical system of the optical adaptor and an image pick-up device.

18 Claims, 14 Drawing Sheets

MEASURING ENDOSCOPE APPARATUS

This application claims benefit of Japanese Application No. 2001-162869 filed on May 30, 2001, the contents of which are incorporated by this reference.

BACKGROUND OF THE INVENTION

1. Field of the Invention

The present invention relates to a measuring endoscope apparatus and, more particularly, to a measuring endoscope apparatus in which a plurality of optical adaptors can be replaced to use at the tip of an insertion portion of the endoscope.

2. Description of the Related Art

In general, the detailed examination of a subject by using an endoscope requires the measuring of the position of the subject. To satisfy this request, conventionally, various measuring apparatuses using the endoscope are proposed.

For example, a proposal disclosed in Japanese Unexamined Patent Application Publication No. 10-248806 shows a measuring endoscope apparatus for stereo measuring.

Further, a proposal disclosed in Japanese Patent Application No. 2000-101122 by the applicant of the present invention shows a measuring endoscope apparatus which automatically selects and executes measuring methods varied depending on the type of optical adaptor.

In the measuring endoscope apparatus disclosed in the former Japanese Unexamined Patent Application Publication No. 10-248806, an optical adaptor having two optical systems necessary for capturing the image of a subject for measuring is detachably arranged in a main body of an endoscope. Two images through two lens systems in the optical adaptor are formed on one image pick-up device and at least the obtained image through the endoscope is subjected to the image processing, thus performing the measuring of the subject. The measuring endoscope apparatus comprises measuring means which executes processing for reading information from a recording medium on which optical data of the optical adaptor is recorded, processing for correcting the optical data based on a position error of an image pick-up system of the main body of the endoscope, processing for a coordinate transformation of a measuring targeted image based on the corrected optical data, and processing for obtaining three-dimensional coordinates at an arbitrary point by matching two images based on the two coordinate-transformed images.

In the measuring endoscope apparatus having the above-mentioned structure, the three-dimensional coordinates are obtained at the arbitrary point of the subject by matching the two images based on two pieces of image information which are obtained by a coordinate transformation of two images of the subject, that is, captured by the image pick-up device via the optical adaptor. Consequently, the measuring endoscope apparatus can be realized with low price and excellent measuring precision.

The above-mentioned measuring endoscope apparatus is a measuring endoscope apparatus which mainly performs stereo measuring. In addition, the measuring endoscope apparatus can execute comparison and measurement by attaching a detachable normal optical adaptor having a single optical system to the tip of the same endoscope and using an image obtained by the normal optical adaptor.

On the other hand, as disclosed in the latter Japanese Patent Application No. 2000-101122, there are provided the measuring endoscope apparatus comprising a connecting portion provided at the tip of the endoscope, a plurality of types of optical adaptor detachable to the connecting portion, for forming a subject image on an image pick-up device, which performs the measurement by connecting one type of optical adaptor and by performing image processing for an image signal obtained by the image pick-up device, wherein measuring endoscope apparatus further comprises menu display means that performs menu display processing for selecting operation based on display data previously associated with the plurality of optical adaptors and performs measurement based on the selected result in the menu display processing.

In those conventional measuring endoscope apparatuses, the optical adaptor is selected on the menu, thereby a measuring method corresponding to the selected optical adaptor is automatically selected. The measuring can be executed corresponding to the selected measuring method only by pressing a measuring executing switch provided for an endoscope operating portion, in the case of executing the measurement.

In an embodiment disclosed in Japanese Patent Application No. 2000-101122, images of the plurality of optical adaptors are subjected to calibration. The resultant images are stored in a memory card of compact flash (trade mark) as an external storage medium, as data on a measurement environment. In the disclosed structure, by selecting the optical adaptor used on the menu, the data on the measurement environment is selected and used corresponding to the selected optical adaptor.

In the above-disclosed technologies, the measurement based on a stereo image needs processing (calibration) in which a positional relationship between the image pick-up device and the plurality of optical systems provided for the image pick-up device is accurately grasped in advance and the difference of the positional relationship is corrected. However, when attaching the optical adaptor, in an optical-adaptor-replacing-type stereo endoscope, the position varies depending on the attachment of the optical adaptor when hitching the optical adaptor to the tip of the endoscope and, in accordance therewith, the positional relationship between the image pick-up device and the optical system of the optical adaptor might vary. In this case, the difference between the positional relationship between the image pick-up device and the optical system to which the optical adaptor is attached and the previously-performed calibration result might cause the decrease in measuring precision. In order to prevent the decrease in measuring precision, there is a method in which the calibration is performed every time the optical adaptor is attached. However, the calibration on every attachment of the optical adaptor requires complicated processing sequence. A processing capacity of microprocessors used for the current measuring endoscope takes a long time for the calibration.

Further, when a plurality of optical adaptors are provided and the measurement is performed by exchanging the optical adaptors, the measurement can easily be performed by storing the calibration result which is executed for every optical adaptor, as the data on the measurement environment, and switching the data on the measurement environment when exchanging the optical adaptor. However, the measurement might be implemented in a state in which the optical adaptor mismatches the data on the measurement environment stored as the calibration result because only the optical adaptor is replaced and the data on the measurement environment is not selected. This might decrease the measuring precision.

SUMMARY OF THE INVENTION

The present invention is devised in consideration of the above-mentioned problems. It is an object of the present invention to provide a measuring endoscope apparatus which can prevent the measuring that might cause the decrease of precision due to the change in positional relationship between an optical system of an optical adaptor and an image pick-up device, in the case of measurement using a stored calibration result.

According to the present invention, a measuring endoscope apparatus comprises: an endoscope insertion portion having an image pick-up unit for observation at a tip thereof; a processing unit provided on a proximal end side of the endoscope insertion portion, for receiving an image pick-up signal from the image pick-up unit, processing it, and generating a video signal; a display device for receiving and displaying the video signal from the processing unit; and a connecting portion for detachably connecting at the tip of the endoscope insertion portion, a plurality of types of optical adaptor having an observation optical system for forming an observation image to the image pick-up unit. Further, the processing unit comprises: an extracting unit for extracting first information on a positional relationship of the optical adaptor by performing an image processing for a signal transmitted from the image pick-up unit upon image pick-up of a predetermined subject; a storing unit for storing the first information on the positional relationship; a comparing and determining unit for comparing the first information on the positional relationship stored in the storing unit with second information on the positional relationship which is extracted again by the extracting unit; and a notifying unit for notifying a determination result based on determination information from the comparing and determining unit.

The above and other objects, features and advantages of the invention will become more clearly understood from the following description referring to the accompanying drawings.

DESCRIPTION OF THE PREFERRED EMBODIMENTS

Hereinbelow, embodiments of the present invention will be described with reference to the drawings.

(First Embodiment)

Figure 1:
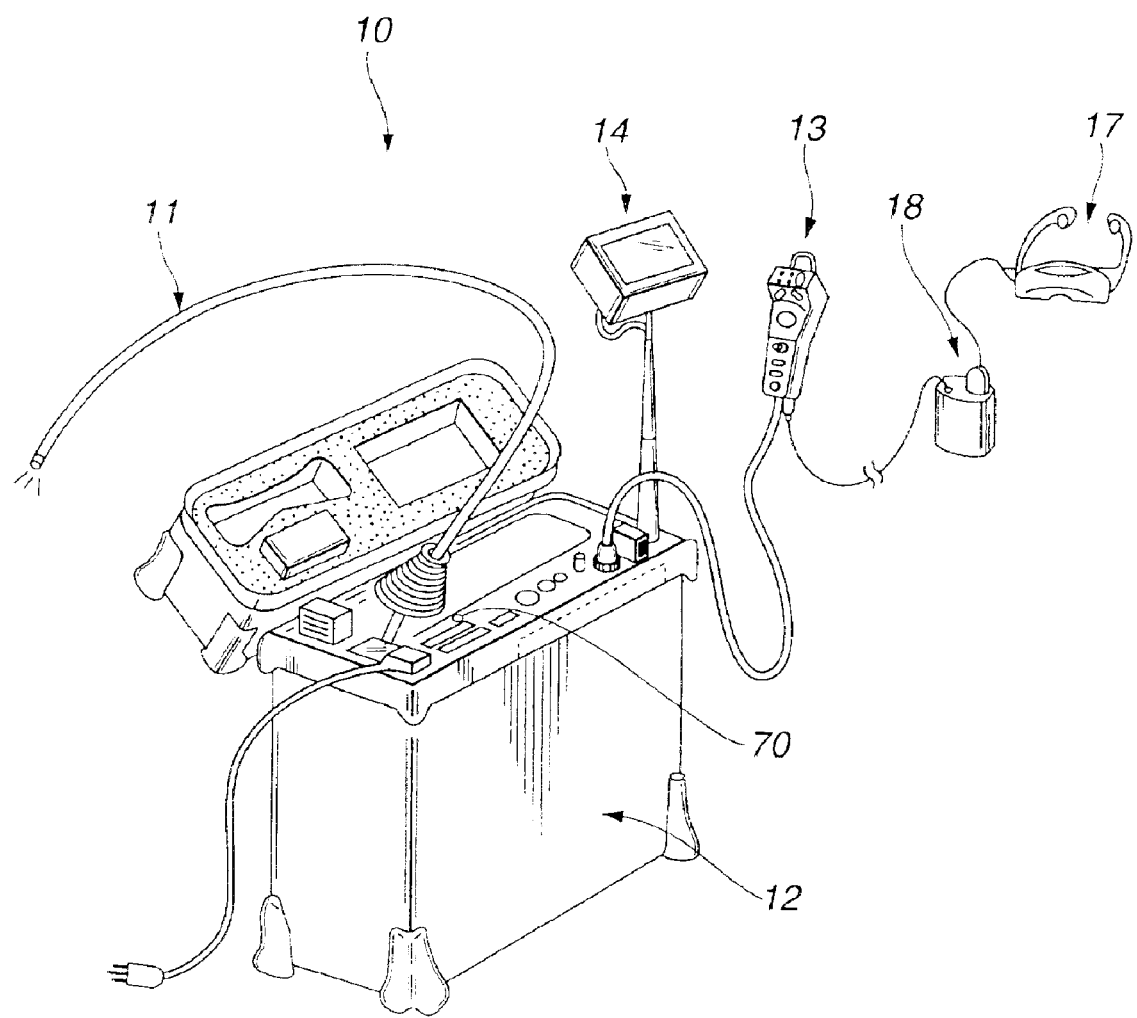
FIG. 1 is a diagram schematically showing the structure of a measuring endoscope apparatus according to a first embodiment of the present invention.
Figure 2:
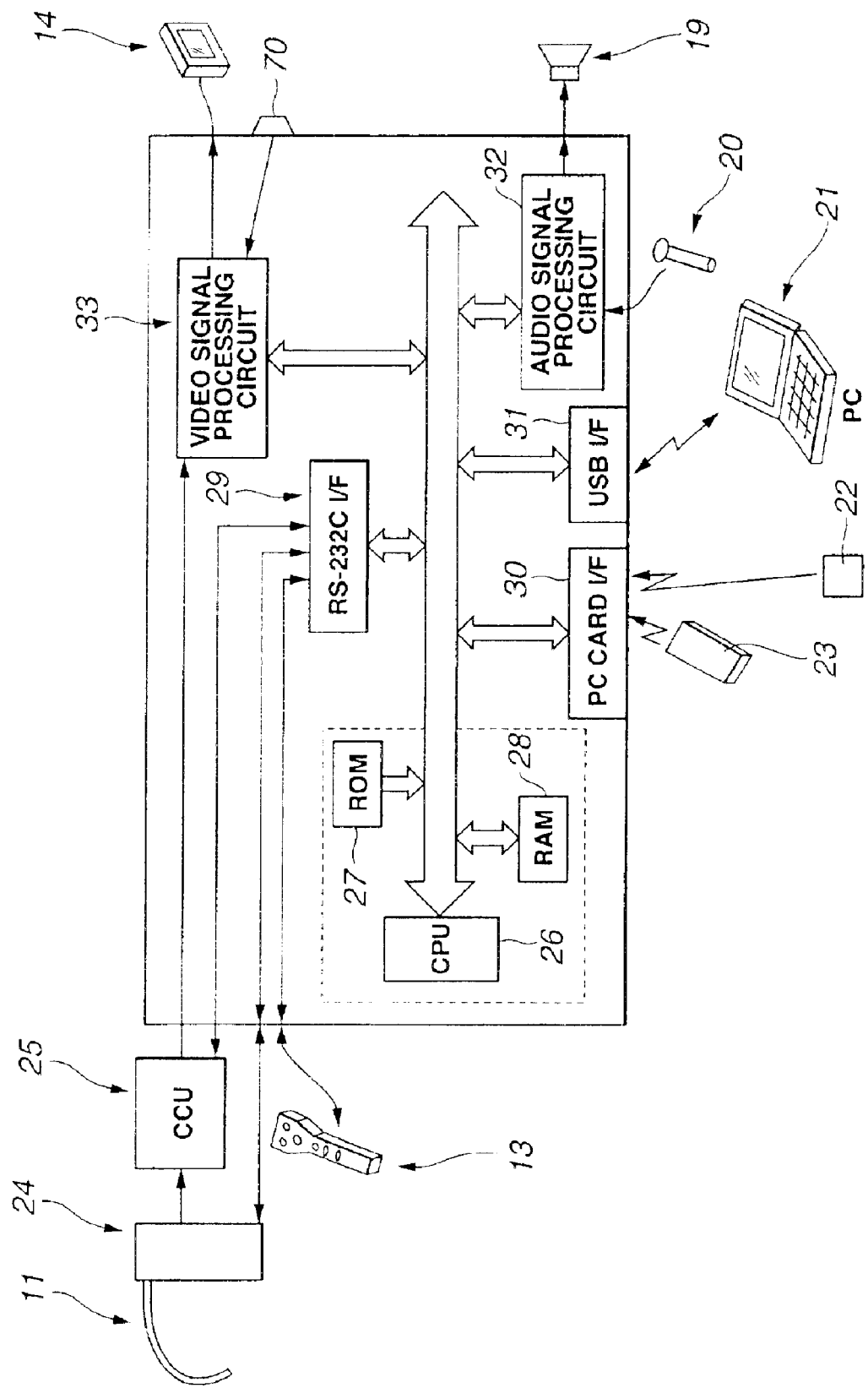
FIG. 2 is a block diagram showing the structure of circuitries in the measuring endoscope apparatus in FIG. 1.
Figure 3:
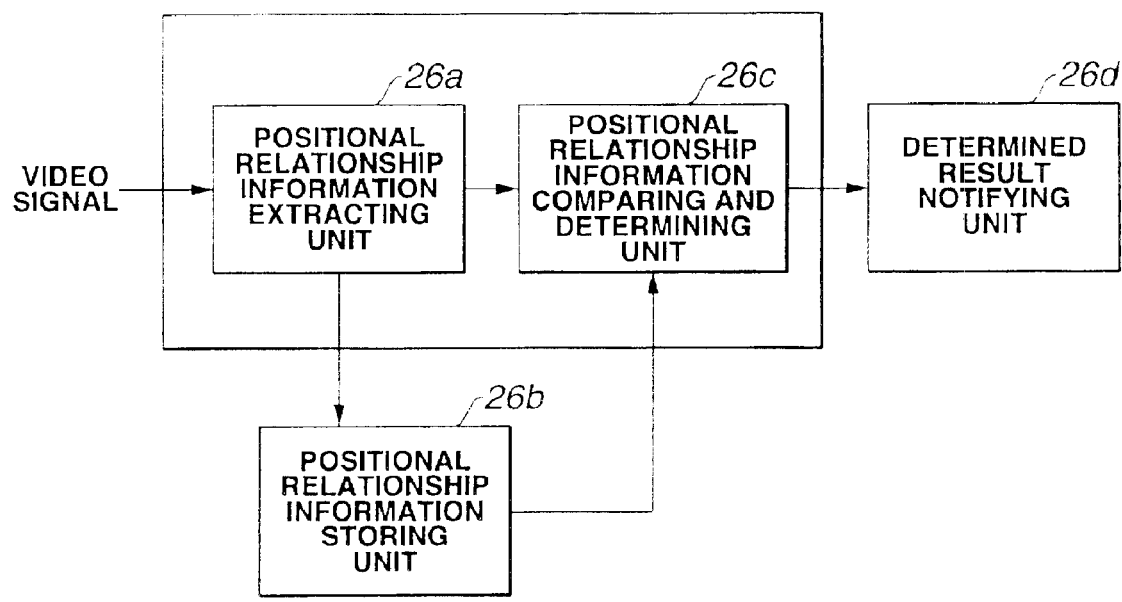
FIG. 3 is a block diagram showing the structure of the processing by a CPU in FIG. 2.
Figure 4:
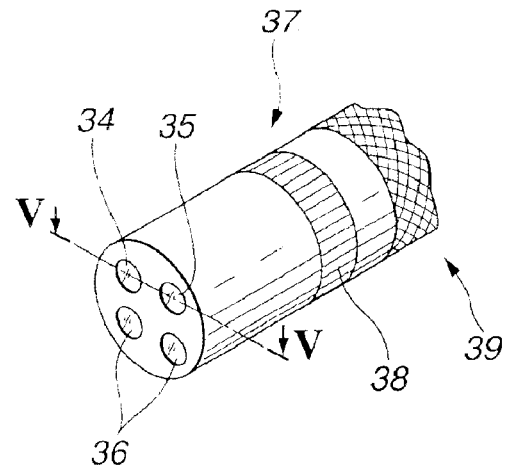
FIG. 4 is a perspective view showing the structure of the tip of an endoscope in FIG. 1, to which a stereo optical adaptor is attached.
Figure 5:
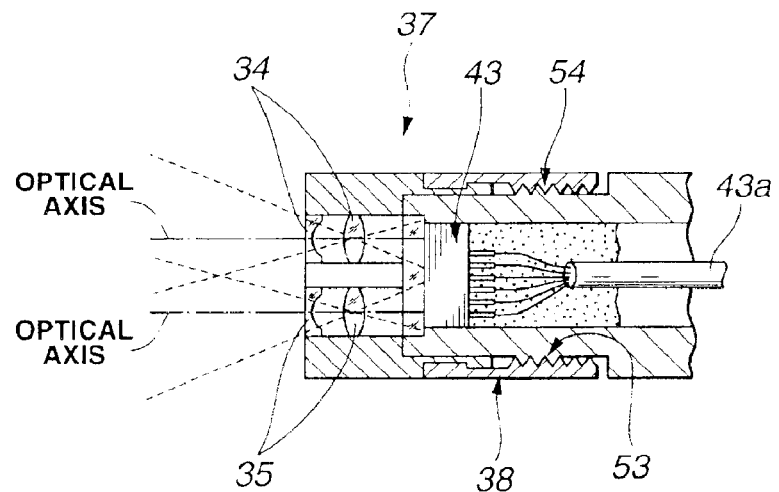
FIG. 5 is a sectional view of a V—V cut-plane in FIG. 4.
Figure 6:
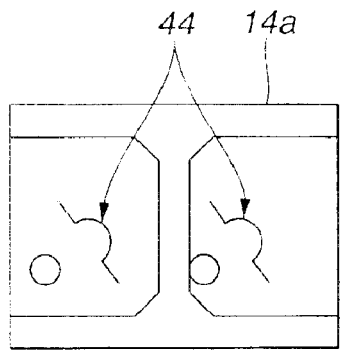
FIG. 6 is a diagram showing an endoscopic image in the case of attaching the stereo optical adaptor in FIG. 4.
Figure 7:
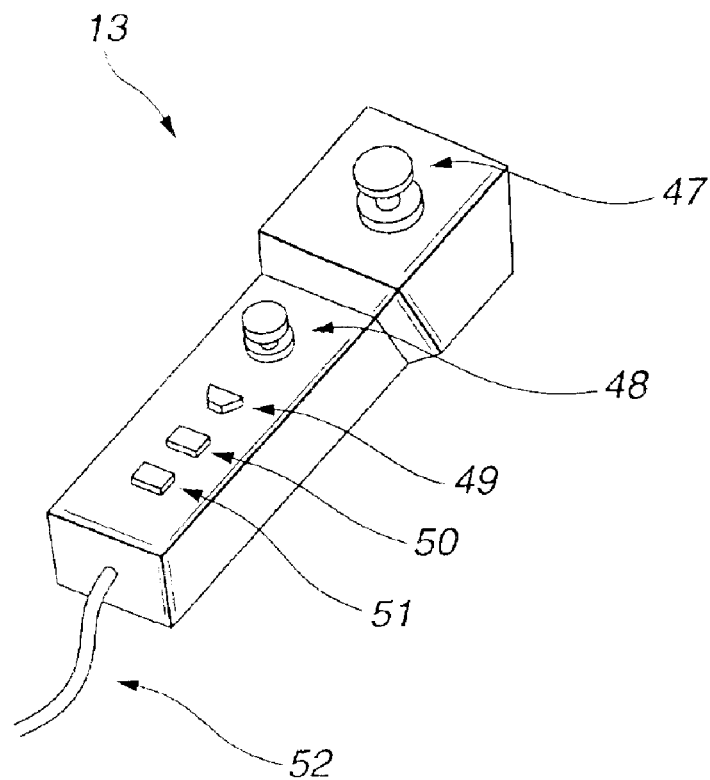
FIG. 7 is a perspective view showing the structure of a remote controller in FIG. 1.
Figure 8:
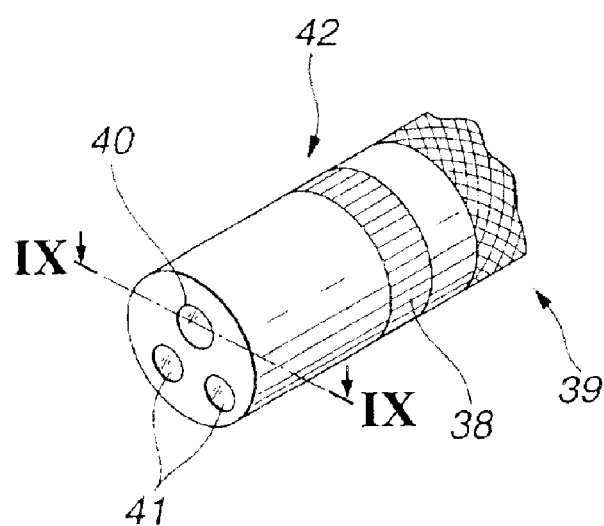
FIG. 8 is a perspective view showing the structure of the tip of the endoscope in FIG. 1, to which a normal optical adaptor is attached.
Figure 9:
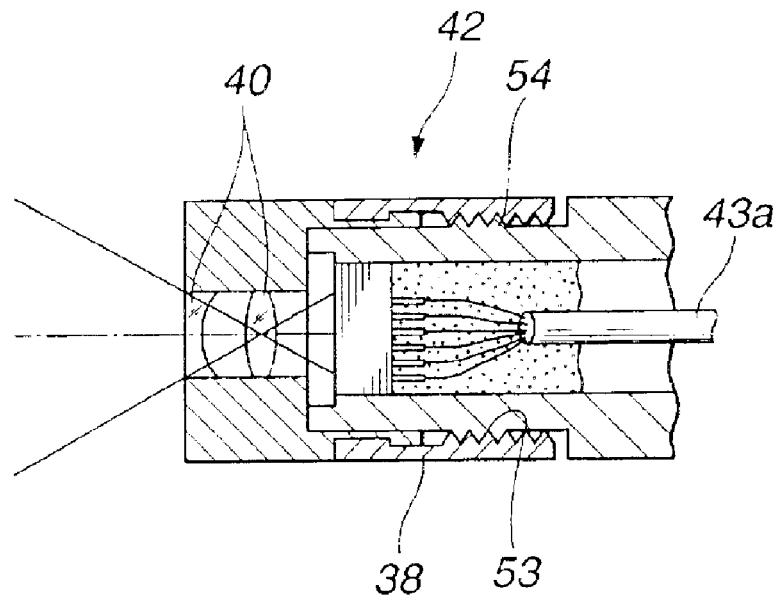
FIG. 9 is a sectional view of a IX—IX cut-plane in FIG. 8.
Figure 10:
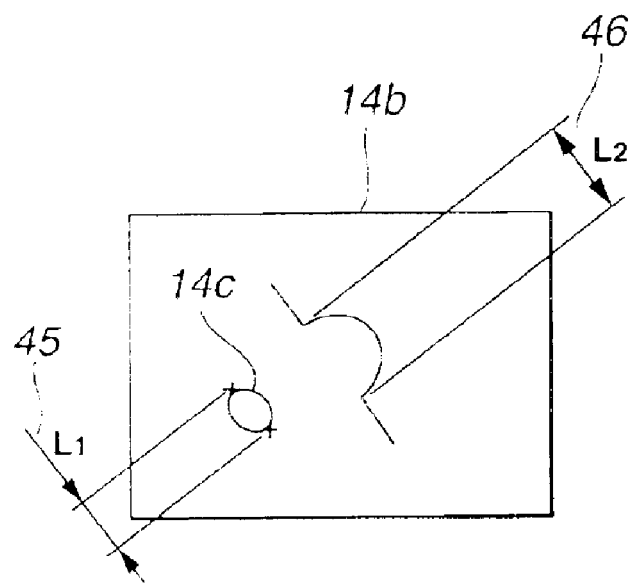
FIG. 10 is a diagram showing an endoscopic image in the case of attaching the normal optical adaptor in FIG. 8.
Figure 11:
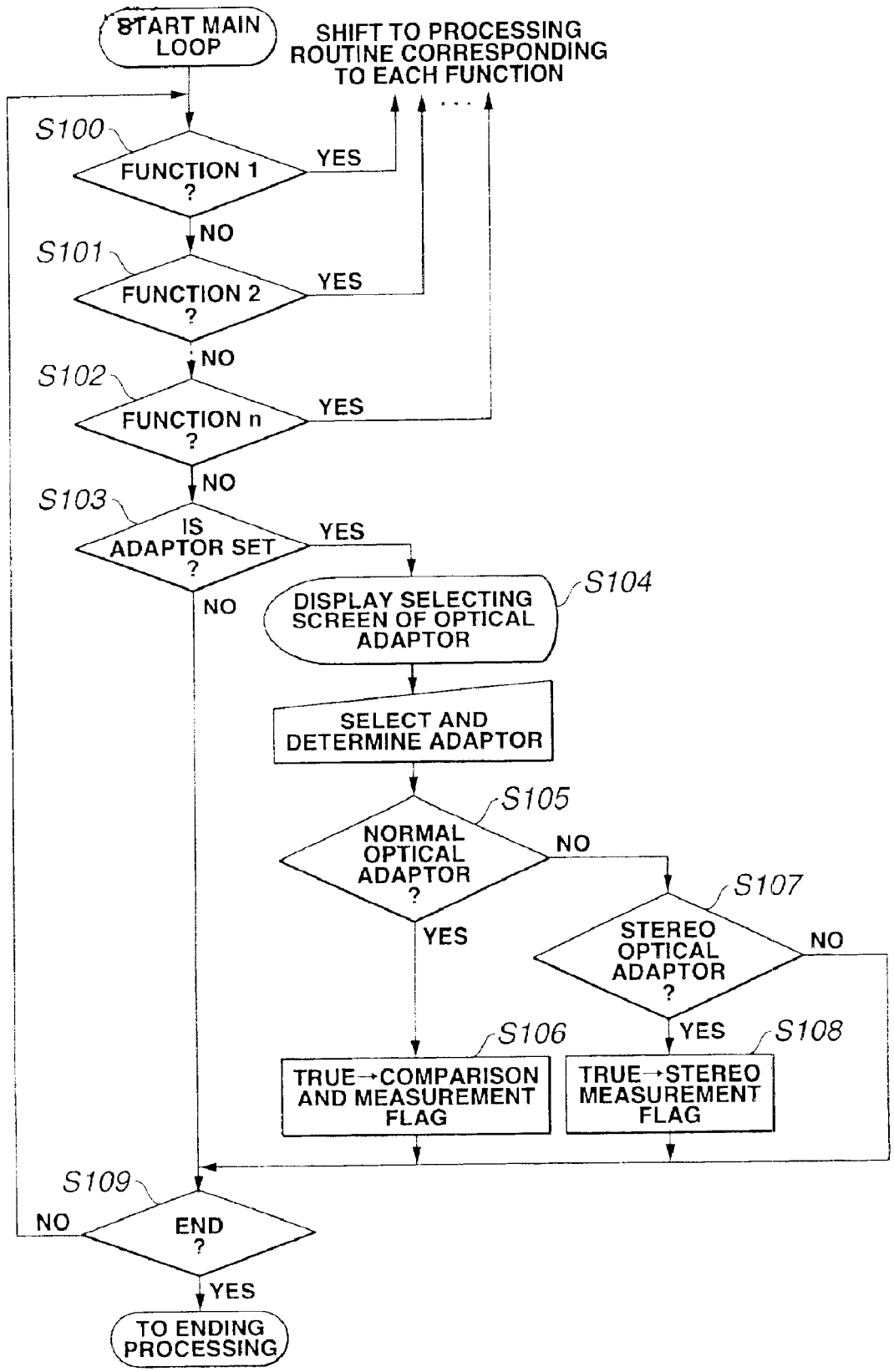
FIG. 11 is a first flowchart showing an example of the control operation by the CPU in FIG. 1 characterized by the first embodiment.
Figure 12:
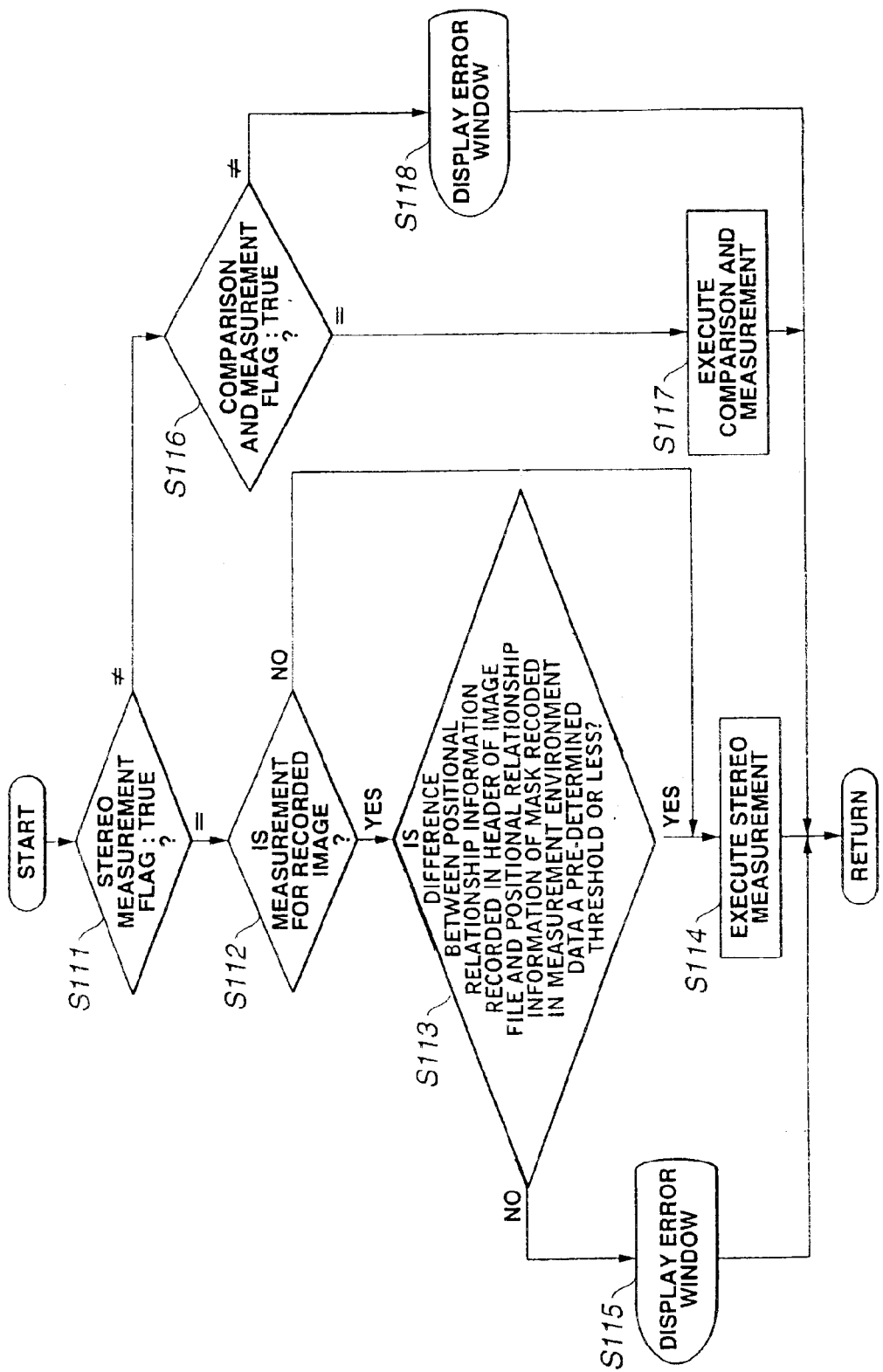
FIG. 12 is a second flowchart showing an example of the control operation by the CPU in FIG. 1 characterized by the first embodiment.
Figure 13:
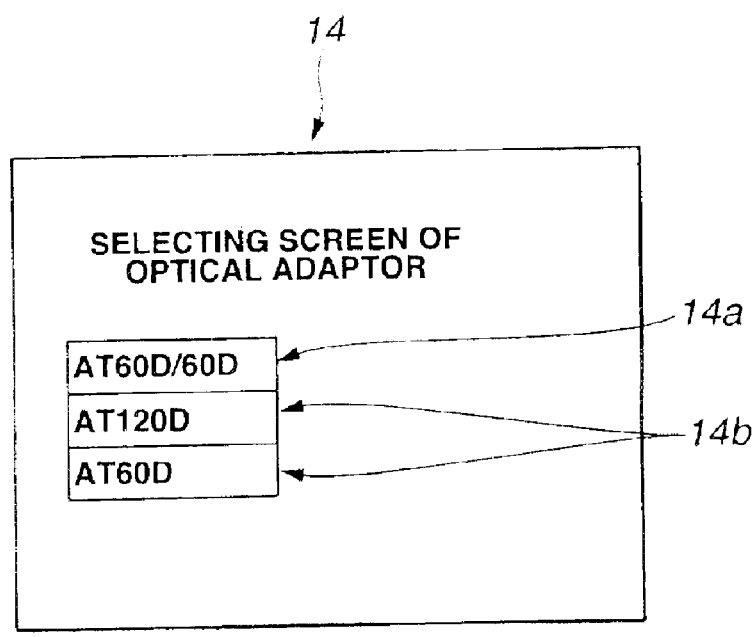
FIG. 13 is a diagram showing an example of a screen for selecting an optical adaptor displayed on an LCD in FIG. 1.
Figure 14:
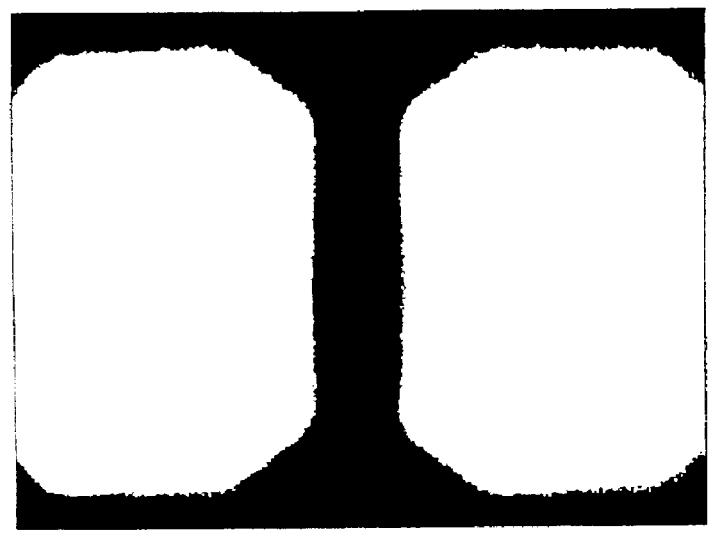
FIG. 14 is a diagram showing images of the shape of a mask of the stereo optical adaptor in FIG. 4.

FIGS. 1 to 14 are diagrams for explaining a measuring endoscope apparatus according to a first embodiment of the present invention. FIG. 1 is a perspective view showing the system structure of the measuring endoscope apparatus according to the first embodiment of the present invention, FIG. 2 is a block diagram showing the structure of circuitries in the measuring endoscope apparatus in FIG. 1, FIG. 3 is a block diagram showing the structure of the processing of a CPU in the measuring endoscope apparatus in FIG. 2, FIG. 4 is a perspective view showing the structure of the tip of an endoscope, to which a stereo optical adaptor is attached, FIG. 5 is a sectional view of a V—V cut-plane in FIG. 4, FIG. 6 is an explanatory diagram showing an endoscopic image in the case of attaching the stereo optical adaptor, FIG. 7 is a perspective view showing the structure of a remote controller, FIG. 8 is a perspective view showing the structure of the tip of the endoscope, to which a normal optical adaptor is attached, FIG. 9 is a sectional view of a IX—IX cut-plane in FIG. 8, FIG. 10 is an explanatory diagram showing an endoscopic image in the case of attaching the normal optical adaptor, FIG. 11 is a first flowchart showing an example of the control operation by the CPU in the measuring endoscope apparatus characterized by the first embodiment, FIG. 12 is a second flowchart showing an example of the control operation by the CPU in the measuring endoscope apparatus characterized by the first embodiment, FIG. 13 is a diagram showing an example of a screen for selecting an optical adaptor displayed on an LCD, and FIG. 14 is a diagram showing images of the shape of a mask of the stereo optical adaptor.

The system structure of a measuring endoscope apparatus 10 will be described according to the first embodiment with reference to FIG. 1.

Referring to FIG. 1, the measuring endoscope apparatus 10 comprises an endoscope insertion portion 11, a control unit 12, a remote controller 13, a liquid crystal monitor (hereinafter, referred to as an LCD) 14, a face mounted display (hereinafter, referred to as an FMD) 17, and an FMD adaptor 18. At least two types of optical adaptors, stereo measurement and normal measurement, are detachably attached at the tip of the endoscope insertion portion 11. The control unit 12 encloses the endoscope insertion portion 11. The remote controller 13 performs necessary operations for executing various control operations of the entire system of the measuring endoscope apparatus 10. The LCD 14 displays an endoscopic image, contents of the control operation (e.g., processing menu), etc. On the FMD 17, a normal endoscopic image can be viewed or it can be stereo-viewed as a pseudo stereo image. The FMD adaptor 18 supplies the image data to the FMD 17.

Next, the system structure of the measuring endoscope apparatus 10 will be described in detail with reference to FIG. 2.

Referring to FIG. 2, the endoscope insertion portion 11 is connected to an endoscope unit 24. The endoscope unit 24 is arranged in, for example, the control unit 12 shown in FIG. 1. Further, the endoscope unit 24 comprises a light source device for obtaining illumination light necessary for photographing and an electric bending device for electrically bending the endoscope insertion portion 11 freely.

An image pick-up signal from a solid image-pick-up device 43 (refer to FIG. 5) at the tip of the endoscope insertion portion 11 is inputted to a camera control unit (hereinafter, referred to as a CCU) 25. The CCU 25 converts the supplied image pick-up signal into a video signal such as an NTSC signal, and supplies the converted signal to main processing circuits in the control unit 12.

As shown in FIG. 2, the main circuits provided in the control unit 12 include: a central processing unit (CPU) 26 for controlling the execution and operation of various functions based on a main program, a ROM 27, a RAM 28, a PC card interface (hereinafter, referred to as a PC card I/F) 30, a USB interface (hereinafter, referred to as a USB I/F) 31, an RS-232C interface (hereinafter, referred to as an RS-232C I/F) 29, an audio signal processing circuit 32, and a video signal processing circuit 33.

The RS-232C I/F 29 is connected to the CCU 25, the endoscope unit 24, and the remote controller 13. The remote controller 13 controls and instructs the operation of the CCU 25 and the endoscope unit 24. The RS-232C I/F 29 performs the communication necessary for controlling the operation of the CCU 25 and the endoscope unit 24 based on the operation of the remote controller 13.

The USB I/F 31 is an interface for electrically connecting the control unit 12 and a personal computer 21. When the control unit 12 and the personal computer 21 are connected via the USB I/F 31, various control operations by instructions such as that for displaying the endoscopic image and that for image processing upon measuring by the control unit 12 can be implemented via the personal computer 21. Further, control information and data necessary for various processing can be received and transmitted between the control unit 12 and the personal computer 21.

A PCMCIA memory card 22 and a compact flash (trade mark) memory card 23 can be detachably connected to the PC card I/F 30. That is, when any memory card is attached, the control unit 12 can read data on control processing information or image information which is stored in the memory card as a recording medium and fetch the read data in the control unit 12 via the PC card I/F 30, or can supply and record the data on the image information or on the control processing information to the memory card via the PC card I/F 30, under the control of the CPU 26.

The video signal processing circuit 33 combines and processes a video signal from the CCU 25 and a display signal based on an operation menu, generated under the control of the CPU 26, so as to display a combined image obtained by combining the endoscopic image supplied from the CCU 25 and the operation menu graphically displayed such as a character, a picture, or a symbol. Further, the video signal processing circuit 33 supplies a video signal subjected to processing necessary for displaying the data on the LCD 14 thereto. Thus, the combined image of the endoscopic image and the operation menu is displayed on the LCD 14. Incidentally, the video signal processing circuit 33 can perform processing for single displaying of an image of the endoscopic image or of the operation menu etc.

An external video input terminal 70 for inputting a video signal to the video signal processing circuit 33 not via the CCU 25 is separately provided for the control unit 12 shown in FIG. 1. When the video signal is inputted to the external video input terminal 70, the video signal processing circuit 33 outputs a combined image of the video signal from the external video input terminal 70, prior to outputting the endoscopic image from the CCU 25.

An audio signal which is collected and generated by a microphone 20 and is recorded to the recording medium such as the memory card, an audio signal which is obtained by reading a signal on the recording medium such as the memory card, or an audio signal generated by the CPU 26 is supplied to the audio signal processing circuit 32. The audio signal processing circuit 32 subjects the supplied audio signal to processing necessary for reproducing the supplied signal (amplification), and outputs the audio signal to a speaker 19. As a consequence, the audio signal is reproduced by the speaker 19.

The CPU 26 executes a program stored in the ROM 27, and performs the operation control of the entire system by controlling various circuit units so as to execute processing corresponding to each purpose.

The remote controller 13 comprises a joy stick 47, a lever switch 48, a freeze switch 49, a store switch 50, and a measurement executing switch 51, as shown in FIG. 7, which are provided together on at least the upper surface of a casing. Reference numeral 52 denotes a signal cable.

In the remote controller 13, the joy stick 47 is a switch for a bending operation of the tip of the endoscope, and can freely instruct the operation in any direction with an angle of 360°. The lever switch 48 is a switch for moving a pointer when various menu operations are graphically displayed or the measurement is performed, and is formed in an almost similar shape with the joy stick 47. The freeze switch 49 is a switch which is used when displaying a moving picture of the endoscope displayed on the LCD 14 as a still image. The store switch 50 is a switch which is used when recording the still image to the PCMCIA memory card 22 (refer to FIG. 2), in the case of displaying the still image by pressing the freeze switch 49. The measurement executing switch 51 is a switch which is used when a software program for measuring is executed.

Incidentally, the freeze switch 49, the store switch 50, and the measurement executing switch 51 are on/off type pressing switches.

The processing contents executed by the CPU 26 will be described with reference to FIG. 3. The measuring endoscope apparatus 10 comprises a positional relationship information extracting unit 26a for extracting information on the positional relationship based on the supplied video signal, a positional relationship information storing unit 26b for receiving the information on the positional information from the positional relationship information extracting unit 26a and storing the information on the positional relationship, a positional relationship information comparing and determining unit 26c for receiving first information on the positional relationship from the positional relationship information storing unit 26b and second information on the positional relationship from the positional relationship information extracting unit 26a and comparing the first and second information on the positional relationship, and a determined result notifying unit 26d for sending a determined result based on the comparison result.

Next, a description is given of the structure of the stereo optical adaptor as one type of the optical adaptors used for the measuring endoscope apparatus 10 according to the first embodiment with reference to FIGS. 4 to 6.

Referring to FIGS. 4 and 5, a stereo optical adaptor 37 is attached to a tip 39 of the endoscope. The stereo optical adaptor 37 is fixed by being screwed to external threads 54 of the tip 39 of the endoscope by using internal threads 53 of a fixing ring 38.

A pair of illumination lenses 36 and two objective lens systems 34 and 35 are mounted on the tip of the stereo optical adaptor 37. The two objective lenses 34 and 35 form two images on the image pick-up device 43 arranged in the tip 39 of the endoscope. An image pick-up signal obtained by the image pick-up device 43 is supplied to the CCU 25 via an electrically connected signal line 43a and the endoscope unit 24 shown in FIG. 2. The CCU 25 converts the supplied signal into a video signal and thereafter supplies the resultant signal to the video signal processing circuit 33. Thus, for example, an image 14a as shown in FIG. 6 is displayed on the screen of the LCD 14.

According to the first embodiment, the measuring endoscope apparatus 10 executes the stereo measurement of a subject as a measuring target based on optical data from the recording medium, such as the compact flash memory card, on which the optical data from the stereo optical adaptor 37 is recorded, by using the endoscopic image 14a shown in FIG. 6.

The stereo measurement of the measuring endoscope apparatus 10 is performed by executing at least: first processing for reading optical information from the recording medium, such as the compact flash memory card, on which the optical data from the stereo optical adaptor 37 is recorded; second processing for reading the information on the positional relationship between the image pick-up device 43 in the tip 39 of the endoscope and the objective lens systems 34 and 35 in the stereo optical adaptor 37; third processing for obtaining a position error of the image pick-up device 43 in the measuring endoscope apparatus based on the read information on the positional relationship and main information on the positional relationship between the image pick-up device 43 in the endoscope and the objective lens systems 34 and 35 in the stereo optical adaptor 37 obtained upon manufacturing; fourth processing for correcting the optical data based on the position error; fifth processing for coordinate transformation of an image to be subjected to the measurement based on the corrected optical data; and sixth processing for obtaining three-dimensional coordinates at an arbitrary point by matching two images based on the coordinate-transformed image.

The CPU 26 subjects the stereo optical adaptor 37 to, for example, the first to fourth processing once, and controls the operation so that the processing results are recorded to the compact flash memory card 23 as data on the measurement environment. The first to fourth processing is called calibration. In this case, information on the date on which the calibration is executed is recorded to the compact flash memory card 23 as a part of the data on the measurement environment. Upon executing the stereo measurement after that, the CPU 26 controls the operation for loading the data on the measurement environment to the RAM and then executing the fifth and sixth processing.

The second processing for reading the information on the positional relationship between the image pick-up device 43 in the tip 39 of the endoscope and the objective lens systems 34 and 35 in the stereo optical adaptor 37 is performed by capturing the shape of a mask provided for the stereo optical adaptor and comparing the mask shape and mask position upon manufacturing, as shown in FIG. 14. In this case, the mask shape is obtained by capturing a white image (e.g., reflecting a white sheet). The brightness of the white image in this case is determined depending on the gain of the CCU 25 and the shutter speed.

Ordinarily, the gain of the CCU 25 and the shutter speed of the image pick-up device 43 are automatically controlled so as to match the best condition. However, when capturing the mask shape, the gain of the CCU 25 is set to be low and the shutter speed of the image pick-up device 43 is set to be high and therefore the image is dark and the mask shape cannot be clearly photographed. This gives an adverse influence to the measuring precision. Thus, according to the first embodiment, the gain of the CCU 25 and the shutter speed are fixed under the control of the CPU 26. Accordingly, the mask shape can be captured without fail and the decrease of the measuring precision is prevented.

The data on the measurement environment contains two tables, an optical data table and a coordinate transformation table for correcting the subject image. The optical data table includes the information on the positional relationship between the image pick-up device 43 and the objective lens systems 34 and 35 in the stereo optical adaptor 37, the corrected optical data, the information on the boundary of a field of view of the stereo optical adaptor, and an individual identification number as a copy of a serial number of the endoscope insertion portion 11 stored in the ROM 27. It is controlled so that the data on the measurement environment is recorded to the detachable compact flash memory card 23.

Further, according to the first embodiment, the image is recorded to the PCMCIA memory card 22 under the control of the CPU 26. That is, it is controlled so that the image is recorded to a memory card different from the compact flash memory card 23 for recording the data on the measurement environment.

Upon recording the image, a part of the data on the measurement environment, that is, at least a part of the image including the copy of the information on the positional relationship is recorded as a part of data in an image data file or as another file data associated with the image file. Upon reading the image and starting the measurement, contents of the copy of the data on the information on the positional relationship are compared with the information on the positional relationship in the data on the measurement environment. Then, if the difference as the comparison result is larger than a predetermined threshold, a warning message is displayed on the LCD 14 and the measurement is canceled without starting predetermined measurement.

For example, when performing the measurement of the length of a crack 44 in FIG. 6, a measuring point is designated by a polyline to trace the crack 44 on the left of the screen. The CPU 26 searches for a corresponding point on the right of the screen for every designation of a new measuring point, obtains three-dimensional coordinates at the measuring point based on coordinates of the measuring point and the corresponding point, calculates a distance between two points, a point designated last based on the three-dimensional coordinates and a point designated second last, calculates the sum of the distances, and displays the entire length of the crack 44 on the LCD 14.

Next, a description is given of the structure of the normal optical adaptor used for the measuring endoscope apparatus 10 according to the first embodiment with reference to FIGS. 8 to 10.

FIGS. 8 and 9 show a state in which a normal optical adaptor 42 is mounted on the tip 39 of the endoscope. The normal optical adaptor 42 is fixed by being screwed to the external thread 54 of the tip 39 of the endoscope by using the internal thread 53 of the fixing ring 38.

A pair of an illumination lens 41 and an objective lens system 40 are provided for the tip of the normal optical adaptor 42. The objective lens system 40 forms an image on the image pick-up device 43 arranged in the tip 39 of the endoscope. Similarly to the case of the stereo optical adaptor 37, the obtained image pick-up signal is supplied to the CCU 25 via the electrically connected signal line 43a and the endoscope unit 24. The CCU 25 converts the resultant signal into a video signal and supplies the converted signal to the video signal processing circuit 33. As a consequence, for example, an image 14b shown in FIG. 10 is displayed on the LCD 14.

According to the first embodiment, the measuring endoscope apparatus 10 performs the measurement using the normal optical adaptor by utilizing a comparison and measuring method. Namely, the comparison and measurement are performed by using a known dimension on the screen as a base.

For example, when a diameter of a circle 14c shown in FIG. 10 is known, a pointer is placed at both ends of the diameter of the circle 14c and a length L1 (45) between the two points is inputted. A length to be known L2 (46) is obtained by a ratio through calculation of the CPU 26 based on the size of the length L1 on the screen. In this case, distortion correction is executed based on information on distortion characteristic of the lens so as to obtain the dimension more accurately by adjustment. The distortion characteristic of the lens is previously recorded on the ROM 27, and the CPU 26 implements the comparison and measurement so that data corresponding to the selected normal optical adaptor 42 is loaded to the RAM 28.

As mentioned above, the measuring endoscope apparatus 10 comprises: the endoscope insertion portion 11 having an image pick-up unit for observation (image pick-up device 43) at the tip thereof; a processing unit (the CCU 25, the CPU 26, the ROM 27, the RAM 28, and the video signal processing circuit 33) arranged on the proximal end of the endoscope insertion portion 11, for receiving an image-pickup signal from the image pick-up unit, performing the processing, and generating the video signal; a display device for receiving the video signal from the processing unit and displaying it (the LCD 14); and a connecting portion (the external thread 54) for detachably connecting a plurality of types of the optical adaptors 37 and 42 having an observation optical system for forming an observation image on the image pick-up unit to the tip of the endoscope insertion portion.

The processing unit has: a positional relationship information extracting unit for extracting first information on the positional relationship of the optical adaptor by performing the image processing for a signal transmitted from the image pick-up unit upon capturing the image of a predetermined subject; a positional relationship information storing unit for storing the first information on the positional relationship; a positional relationship information comparing and determining unit; and a determination result notifying unit for notifying the determination result based on determination information from the positional relationship information comparing and determining unit. When the optical adaptor is replaced at the tip of the endoscope insertion portion 11, the positional relationship information comparing and determining unit compares second information on the positional relationship which is extracted again by the positional relationship information extracting unit with the first information on the positional relationship stored in the positional relationship information storing unit, and generates the determination information.

Next, the operation according to the first embodiment will be described.

Hereinbelow, a detailed description is given of the control operation by the CPU 26 in the measuring endoscope apparatus 10 characterized by the first embodiment with reference to FIGS. 11 and 12.

Now, it is assumed that power of the measuring endoscope apparatus 10 shown in FIG. 1 is turned on and is used. Then, the CPU 26 implements initialization of the measuring endoscope apparatus 10, thereafter, executes main program (refer to FIG. 11), and is in a standby mode by a main loop including steps S100, S101, S102, S103, and S109. When functions in steps S100, S101, and S102 are instructed, the CPU 26 shifts to processing of the functions and, when a function in step S103 is instructed, the CPU 26 advances to step S104.

In determination in step S103, the CPU 26 determines whether or not the optical adaptor is attached to the tip 39 of the endoscope and whether or not the setting operation of the optical adaptor is performed. If it is determined that the optical adaptor is not attached, in processing in step S109, the CPU 26 determines whether or not ending operation is executed. If it is determined in step S109 that the ending operation is executed, the CPU 26 starts ending processing. If it is determined that the ending operation is not executed, the CPU 26 returns the processing to step S100.

On the other hand, if it is determined in step S103 that the optical adaptor is attached to the tip 39 of the endoscope and the setting operation of the attached optical adaptor is performed, the CPU 26 shifts the processing to step S104. That is, the CPU 26 enters a standby mode for inputting a function for setting the optical adaptor by shifting the processing to that for displaying the screen for selecting an optical adaptor in step S104.

When any optical adaptor is attached to the tip 39 of the endoscope, the CPU 26 calls the setting function for the optical adaptor and shifts the processing to step S104 whereupon a signal for displaying the screen for selecting an optical adaptor based on the function for setting the optical adaptor by the processing is generated and the generated signal is supplied to the video signal processing circuit 33 (refer to FIG. 2). Accordingly, the CPU 26 displays the screen for selecting an optical adaptor shown in FIG. 13 on the LCD 14. In other words, the screen for selecting an optical adaptor is a display screen for selecting any of an AT60D/60D stereo optical adaptor shown in the image 14a, an AT120D and an AT60D normal optical adaptor shown in the image 14b. A user views the selecting screen and selects the currently used optical adaptor by vertically moving a cursor (not shown) displayed on the screen by using the lever switch 48.

Thereafter, in determination in step S105, the CPU 26 determines whether or not the user's selected optical adaptor is the normal optical adaptor. If it is determined in step S105 that it is the normal optical adaptor, in processing in step S106, the CPU 26 sets a comparison and measuring flag to TRUE, and shifts the processing to the main loop. On the other hand, if it is determined in step S105 that it is not the normal optical adaptor, the CPU 26 shifts the processing to step S107.

In processing in step S107, the CPU 26 determines whether or not the user's selected optical adaptor is the stereo optical adaptor. If it is determined in step S107 that it is the stereo optical adaptor, in processing in step S108, the CPU 26 sets a stereo measuring flag to TRUE and shifts the processing to the main loop. In the main loop, the CPU 26 sets the measuring endoscope apparatus 10 to be in a standby mode for use until the user presses the measurement executing switch 51 of the remote controller 13. If it is determined in step S107 that it is not the stereo optical adaptor, similarly, the CPU 26 controls the operation so that the measuring endoscope apparatus 10 is in the standby mode for the use.

Thereafter, the user presses the measurement executing switch 51 of the remote controller 13 and then the CPU 26 executes a program of a routine shown in FIG. 12.

First, in determination in step S111, the CPU 26 determines whether or not the stereo measuring flag is TRUE. If it is determined that the stereo measuring flag is TRUE, the CPU 26 determines that the stereo measurement is implemented. In processing in step S112, the CPU 26 determines whether or not the recorded image is subjected to the measurement. If it is determined in step S112 that the recorded image is not subjected to the measurement, the CPU 26 shifts to processing in step S114 whereupon the CPU 26 controls the operation so that the above-mentioned stereo measurement is performed. On the other hand, if it is determined that the recorded image is subjected to the measurement, in step S113, the CPU 26 determines whether or not the difference between the information on the positional relationship recorded in a header of the image file and the information on the positional relationship recorded in the data on the measurement environment is a predetermined threshold or less. If it is determined that the difference is the predetermined threshold or less, the CPU 26 returns the processing to step S114 whereupon it controls the operation that the above-mentioned stereo measurement is implemented.

After completing the stereo measurement, the CPU 26 sets the measuring endoscope apparatus 10 to be in the standby mode for the purpose of the display of the measured result or for a re-measuring. If it is determined that the difference is larger than the predetermined threshold, the CPU 26 shifts the processing to step S115 whereupon an error window for notifying the determination result that the measurement cannot be implemented is generated, the window is displayed on the LCD 14, and thereafter the measuring endoscope apparatus 10 is set to the standby mode.

If it is determined in the determination in step S111 that the stereo measurement flag is not TRUE, in determination in step S116, the CPU 26 determines whether or not the comparison and measurement flag is TRUE. If it is determined that the comparison and measurement flag is TRUE, the CPU 26 determines that the normal comparison and measurement are performed. Then, the CPU 26 shifts the processing to step S117 whereupon it controls the operation so that the above-mentioned comparison and measurement are executed. After completing the comparison and measurement, in similar manner to the above-mentioned stereo measurement, the CPU 26 displays the measured result or sets the stereo measuring 10 to be in the standby mode for re-measuring.

On the other hand, if it is determined in step S116 that the comparison and measuring flag is not TRUE, in step S118, the CPU 26 controls the video signal processing circuit 33 so that the error window is generated to notify the determination result that the measurement cannot be implemented. After displaying the error window on the LCD 14, the CPU 26 sets the measuring endoscope apparatus 10 to be in the standby mode.

Upon displaying the error window, a message that the measurement cannot accurately be executed is effectively transmitted to the user by outputting alarm sound from the speaker 19.

More specifically, according to the first embodiment, as mentioned above, the measuring program is implemented corresponding to the stereo measurement flag or the comparison and measurement flag by pressing the measurement executing switch 51 of the remote controller. In particular, when performing the stereo measurement of the recorded image, contents of a copy of the information on the positional relationship associated with the image is compared with the information on the positional relationship of the data on the measurement environment. Then, when the difference is larger than the predetermined threshold, the measurement is not started.

Accordingly, it is possible to prevent an execution of the measuring which might cause the decrease of the precision due to the change in positional relationship.

Incidentally, upon recording the image, a copy of a part including at least the information on the positional relationship of the data on the measurement environment is simultaneously recorded as a part of the image data file. In this case, to cause the same effect, the copy of the part of the data on the measurement environment as to be the part of the image data file is recorded as another file associated with the image file.

The first embodiment has the following advantages.

According to the first embodiment, as mentioned above, upon reading the subject image which is recorded on the storage medium and performing the measuring thereof, the contents of the copy of the information on the positional relationship associated with the subject image are compared with the contents of the information on the positional relationship as a part of the data on the measurement environment. Thereby, it is possible to check the degree of the matching between the image and the stored data on the measurement environment. Further, it is possible to extremely reduce the possibility that the precision of the measurement is decreased, caused by the measuring performed by using the mismatched data on the measurement environment.

(Second Embodiment)

Figure 15:
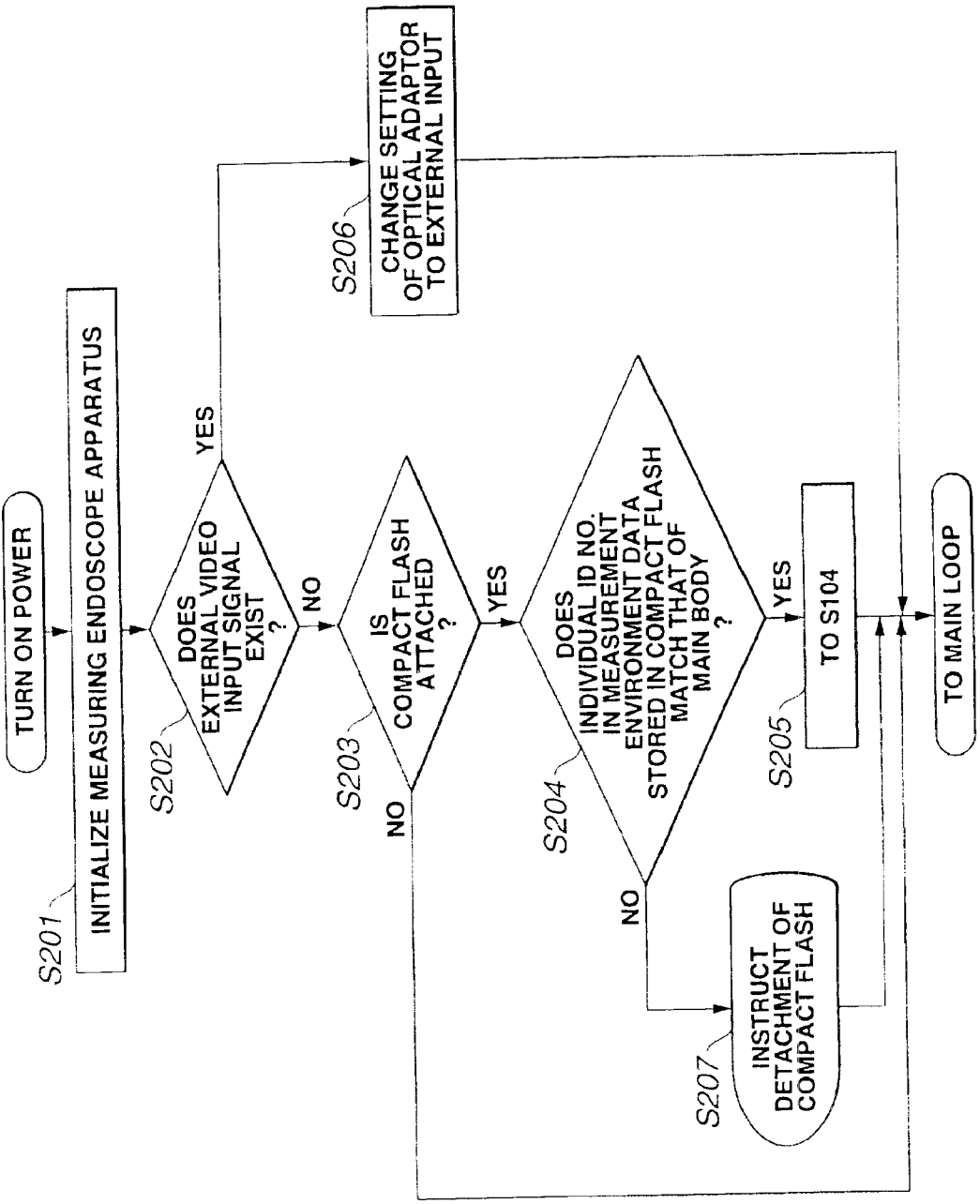
FIG. 15 is a flowchart showing an example of the control operation by a CPU characterized by a second embodiment of the present invention.

FIG. 15 is a flowchart showing an example of the control operation of a CPU in a measuring endoscope apparatus characterized by a second embodiment of the present invention. For the second embodiment, the same components as those according to the first embodiment are described by using those in FIGS. 1 to 14 therefor.

According to the second embodiment, different from the first embodiment, the measuring apparatus additionally has signal detecting means for detecting whether or not a video signal is inputted to an external input terminal 70, changing means for changing the setting of the optical adaptor to an external input when detecting an external video input signal in the external video input terminal 70 upon starting the measuring endoscope apparatus 10, memory card detecting means for detecting whether or not the compact flash memory card 23 for recording the data on the measurement environment is attached to the measuring endoscope apparatus 10, data detecting means for detecting whether or not valid data on the measurement environment is recorded into the compact flash memory card 23, and screen generating means for generating the screen for selecting an optical adaptor shown in FIG. 13 after detecting the valid data on the measurement environment and completing the starting of the measuring endoscope apparatus 10.

According to the second embodiment, other structure is substantially the same as that of the measuring endoscope apparatus 10 according to the first embodiment.

Next, a detailed description is given of the operation according to the second embodiment with reference to FIG. 15.

Now, it is assumed that power of the measuring endoscope apparatus 10 shown in FIG. 1 is turned on and used. Then, as shown in FIG. 15, the CPU 26 initializes the measuring endoscope apparatus 10 in step S201 and thereafter, in processing of step S202, it determines whether or not an external video input signal exists. If it is determined in step S202 that the external video input signal exists, in processing of step S206, the CPU 26 changes the setting of the optical adaptor to an external input, and shifts the processing to the main loop. If it is determined in step S202 that the external input signal does not exist, the CPU 26 shifts the processing to step S203.

In step S203, the CPU 26 determines whether or not the compact flash memory card 23 is attached to the measuring endoscope apparatus 10. If it is determined that the compact flash memory card 23 is attached, in processing of step S204, the CPU 26 determines that an individual identification number in the data on the measurement environment stored in the compact flash memory card 23 matches a value of the ROM 27. If it is determined in step S204 that the individual identification number does not match the value of the ROM 27, the CPU 26 shifts to step S207 whereupon it generates a message instructing the detachment of the compact flash memory card 23, and displays the generated message on the LCD 14.

If it is determined in step S204 that the individual identification number matches the value of the ROM 27, the CPU 26 shifts to step S205 whereupon it shifts to step S104 in FIG. 11. In other words, in this case, the CPU 26 displays the screen for selecting an adaptor in FIG. 13 and, after determining the selection, it shifts to the main loop.

If it is determined in step S203 that the compact flash memory card 23 is not attached, the CPU 26 shifts to the main loop. That is, a user who does not attach the compact flash memory card 23 for storing the data on the measurement environment, namely, a user who does not perform the measuring, can skip a step of selecting an optical adaptor, thereby starting the examination by using the measuring endoscope apparatus 10.

After completely ending the processing shown in FIG. 15, if it is detected that the input of the video signal to the external video input terminal 70 changes from "NO" to "YES", the CPU 26 automatically generates a message window indicating that the selection of an optical adaptor is changed corresponding to the external input, displays the generated message window on the LCD 14, and thereafter changes to an optical adaptor to be selected corresponding to the external input.

After that, if it is detected that the input of the video signal to the external video input signal 70 changes from "YES" to "NO", the CPU 26 displays the screen for selecting an optical adaptor as shown in FIG. 13, and promotes the user to select an optical adaptor. Consequently, according to the second embodiment, it is possible to decrease the possibility to apply the data on the measurement environment of the endoscopic image to the image inputted from external equipment and, as a result, to decrease the possibility for a measuring by using improper data on the measurement environment after detaching the external equipment.

The second embodiment has the following advantages.

As mentioned above, according to the second embodiment, the advantages same as the first embodiment shown in FIGS. 1 to 14 are obtained. Further, when detecting the memory card having the data on the measurement environment for measuring upon starting the measuring endoscope apparatus 10, interlockingly thereto, the screen for selecting an adaptor is displayed and the user is promoted to select the setting of the optical adaptor. Thereby, when the image is recorded when the information on the optical adaptor does not exist, and thereafter, the image is reproduced and a measuring is performed, it is possible to decrease the possibility for deteriorating the measuring precision caused by using the erroneous relationship between the image and the measurement environment. As a result, it is possible to decrease the possibility for the measurement by using the improper data on the measurement environment after detaching the external equipment.

(Third Embodiment)

Figure 16:
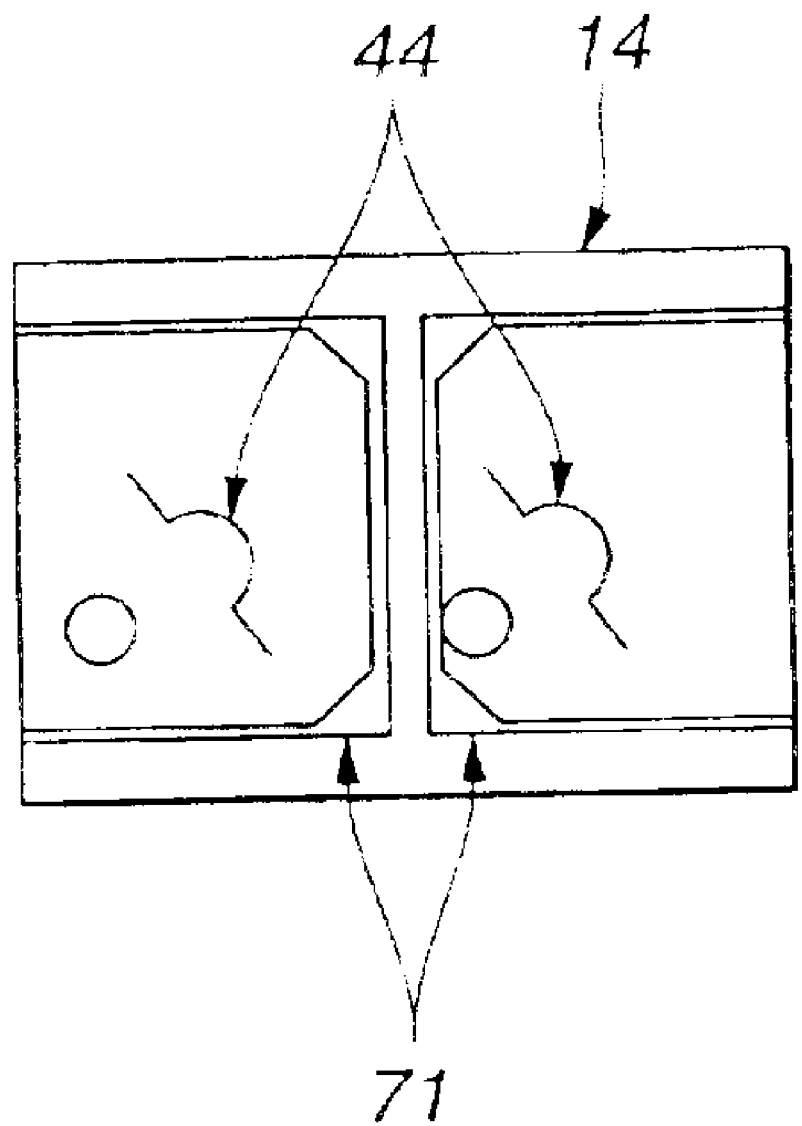
FIG. 16 is a diagram showing an example of information on the boundary of a field of view which is overlapped on a subject image and displayed by an apparatus according to a third embodiment of the present invention.
Figure 17:
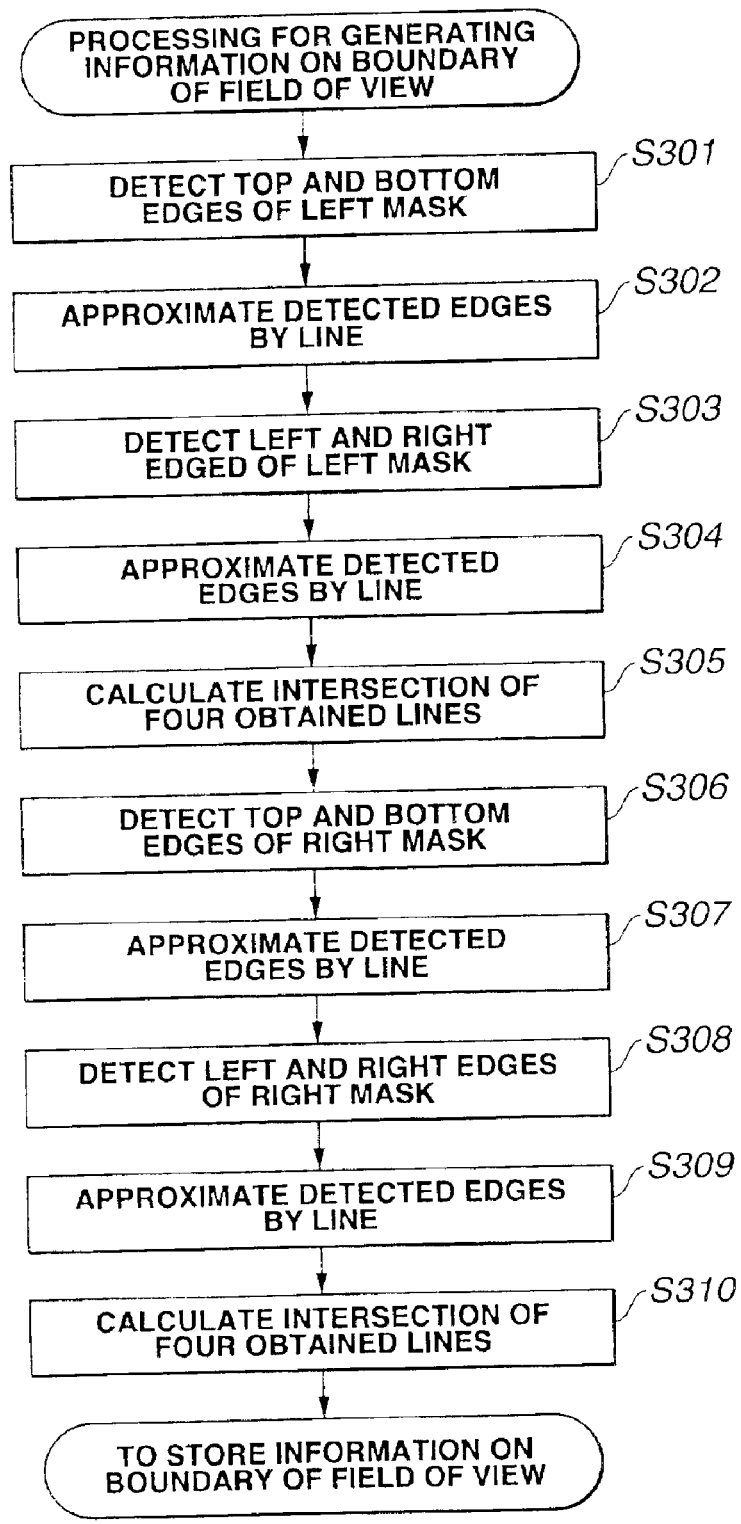
FIG. 17 is a flowchart showing an example of the control operation by a CPU characterized by the third embodiment of the present invention.

FIGS. 16 and 17 are diagrams for explaining a third embodiment of the present invention. FIG. 16 is a diagram showing one example of the measured image upon stereo measurement. FIG. 17 is a flowchart showing an example of the control operation of a CPU in a measuring endoscope apparatus characterized by the third embodiment. According to the third embodiment, the same components as those according to the first embodiment are described by using those in FIGS. 1 to 14 therefor.

According to the third embodiment, different from the first embodiment, the measuring endoscope apparatus further comprises generating means for generating information on the boundary of a field of view of the stereo optical adaptor 37 from the mask shape upon capturing the mask shape in calibration for reading the information on the positional relationship between the image pick-up device 43 at the tip 39 of the endoscope and the objective lens systems 34 and 35 in the stereo optical adaptor 37, storing means for storing the information on the boundary of the field of view as a part of the data on the measurement environment, a menu screen for selecting the execution of the function for displaying an index of the boundary of the field of view during executing the stereo measurement, and screen generating means for generating a screen on which an index of the boundary of the field of view 71 visualized based on the information on the boundary of the field of view in a table of the optical data as shown in FIG. 16 is overlapped on the subject image caused by the execution of the function for displaying the index of the field of view on the menu screen. Other structure is substantially the same as that of the measuring endoscope apparatus 10 according to the first embodiment.

Next, the operation according to the third embodiment will be described.

The mask shape shown in FIG. 14 captured in the calibration shown in the first embodiment shows the shape of the field of view of the stereo optical adaptor 37. Simultaneously, in the case, the information on the boundary of the field of view of the optical adaptor is generated based on the mask shape and the information on the field of view is stored as a part of the data on the measurement environment.

Processing for generating the information on the boundary of the field of view in this case will be described in detail with reference to FIG. 17.

First, referring to FIG. 17, the CPU 26 detects top and bottom edges on a left mask from the captured image in the processing of step S301.

Next, in step S302, the CPU 26 calculates a regression straight line of the detected edges, thereby approximating the top and bottom edges by a straight line.

Next, in steps S303 and S304, the CPU 26 subjects left and right edges on the left mask to the above-mentioned processing, thereby approximating the left and right edges on the left mask by a straight line.

Subsequently, in step S305, the CPU 26 obtains an intersection of the four lines obtained above.

The CPU 26 subjects a right mask to the above-mentioned processing in steps S306, S307, S308, S309, and S310, thereby obtaining eight coordinates for approximating and expressing the mask shape by two quadrilaterals through the above processing.

The CPU 26 stores the eight coordinates in the storing means as a part of the data on the measurement environment. If the function for displaying the information on the boundary of the field of view is selected and executed by a predetermined menu display operation during executing the measuring, the CPU 26 generates an image obtained by overlapping the observed image and the two quadrilaterals, and displays the screen for displaying the information on the boundary of the field of view on the LCD 14 as shown in FIG. 16.

According to the third embodiment, the index of the boundary of the field of view 71 is displayed by the screen for displaying the information on the boundary of the field of view as means for visually checking whether or not the positional relationship between the stereo optical adaptor 37 and the tip 39 of the endoscope is changed through the above-mentioned processing upon executing the calibration and upon capturing the subject image by the user. For example, when the looseness upon attaching the stereo optical adaptor 37 to the tip 39 of the endoscope causes the rotation of the stereo optical adaptor, the index of the boundary of the field of view 71 becomes means for the user to visually check the rotation.

The third embodiment has the following advantages.

As mentioned above, according to the third embodiment, the same advantages as those according to the first embodiment as shown in FIGS. 1 to 14 are obtained. Further, it is possible to check whether or not an error due to the attachment is caused upon attaching the stereo optical adaptor 37 to the measuring endoscope apparatus 10 by the information on the boundary of the field of view 71 which is visualized to the subject image and is overlappingly displayed. Thus, it is possible to further decrease the possibility for decreasing the measuring precision due to such a way of attaching the stereo optical adaptor as causing the mismatch to the data on the measurement environment.

(Fourth Embodiment)

Next, a fourth embodiment will be described. According to the fourth embodiment, the same components as those according to the first embodiment are described by using those in FIGS. 1 to 14 therefor.

According to the fourth embodiment, different from the first embodiment, a mask image upon manufacturing as a part of the optical data (namely, a mask image which is captured by the image pick-up device upon manufacturing) is assumed as a template and the above-mentioned white image is subjected to template matching including the rotation of the template by using the template. Other structure is the same as that of the measuring endoscope apparatus 10 according to the first embodiment.

Reference symbols dx, dy, and $\phi$ denote the information on the positional relationship formed by extracting means, which are stored as the data on the measurement environment. The image is recorded after reading the data on the measurement environment. Therefore, upon recording the image, the information on the positional relationship of the image matches the read data on the measurement environment of the image.

Thereafter, the user executes the calibration again. Then, the information on the positional relationship is newly generated and is recorded as the data on the measurement environment. When the previously-recorded image is read and is subjected to the measurement, the information on the positional relationship recorded into the image is designated by dx1, dy1, and $\phi$1. In this case, the information on the positional relationship recorded into the new data on the measurement environment is designated by dx2, dy2, and $\phi$2. Then, the information on the positional relationship dx1, dy1, and $\phi$1 is compared with the information on the positional relationship dx2, dy2, and $\phi$2.

More specifically, the following processing is implemented as a part of the calibration.

(1) The mask image upon manufacturing as a part of the optical data is set as a template.

(2) The white image is subjected to the template matching, including the rotation of the template, by using the template.

(3) An inclination angle $\phi$ obtained by adding upon manufacturing an inclination of the mask to a rotational angle $\alpha$ of the template having the strongest correlation, the amount of offset to the template in the horizontal direction dx, and the amount of offset to the template in the vertical direction dy are stored as the information on the positional relationship.

Subsequently, the following processing is implemented after reading the recorded image.

(1) The information on the positional relationship which is read from the copy of the data on the information on the positional relationship as a part of the image data file is expressed by the inclination angle $\phi$1, the amount of offset in the horizontal direction dx1, and the amount of offset in the vertical direction dy1.

(2) A straight line having an inclination 1/ tan $\phi$1 and a straight line having tan $\phi$1 passing through a point having the amount of offset in the horizontal direction dx1 and the amount of offset in the vertical direction dy1 from the mask center upon manufacturing are overlapped on the image and the resultant is displayed. Incidentally, when $\phi$1 is 0, a horizontal line and a vertical line passing through the above-mentioned point are displayed.

(3) The information on the positional relationship read from the information on the positional relationship of the data on the measurement environment is expressed by the inclination angle φ2, the amount of offset in the horizontal direction dx2, and the amount of offset in the vertical direction dy2.

(4) A straight line having an inclination 1/tan φ2 and a straight line having tan φ2 passing through a point having the amount of offset in the horizontal direction dx2 and the amount of offset in the vertical direction dy2 from the mask center upon manufacturing are overlapped on the image and the resultant is displayed. Incidentally, when φ2=0, a horizontal line and a vertical line passing through the above-mentioned point are displayed.

The four lines expressed in (2) and (4) represent the indexes of the positional offset. Positional offset generating means generates the four lines based on first information on the positional relationship read from the image and second information on the positional relationship read from the data on the measurement environment. Positional offset information combining means overlaps the four lines on the image and displays the overlapped image.

Accordingly, the difference between the two information on the positional relationship can visually be grasped. Incidentally, the inclination angle and the center of the mask upon manufacturing are stored in the optical data in advance.

(Fifth Embodiment)

Figure 18:
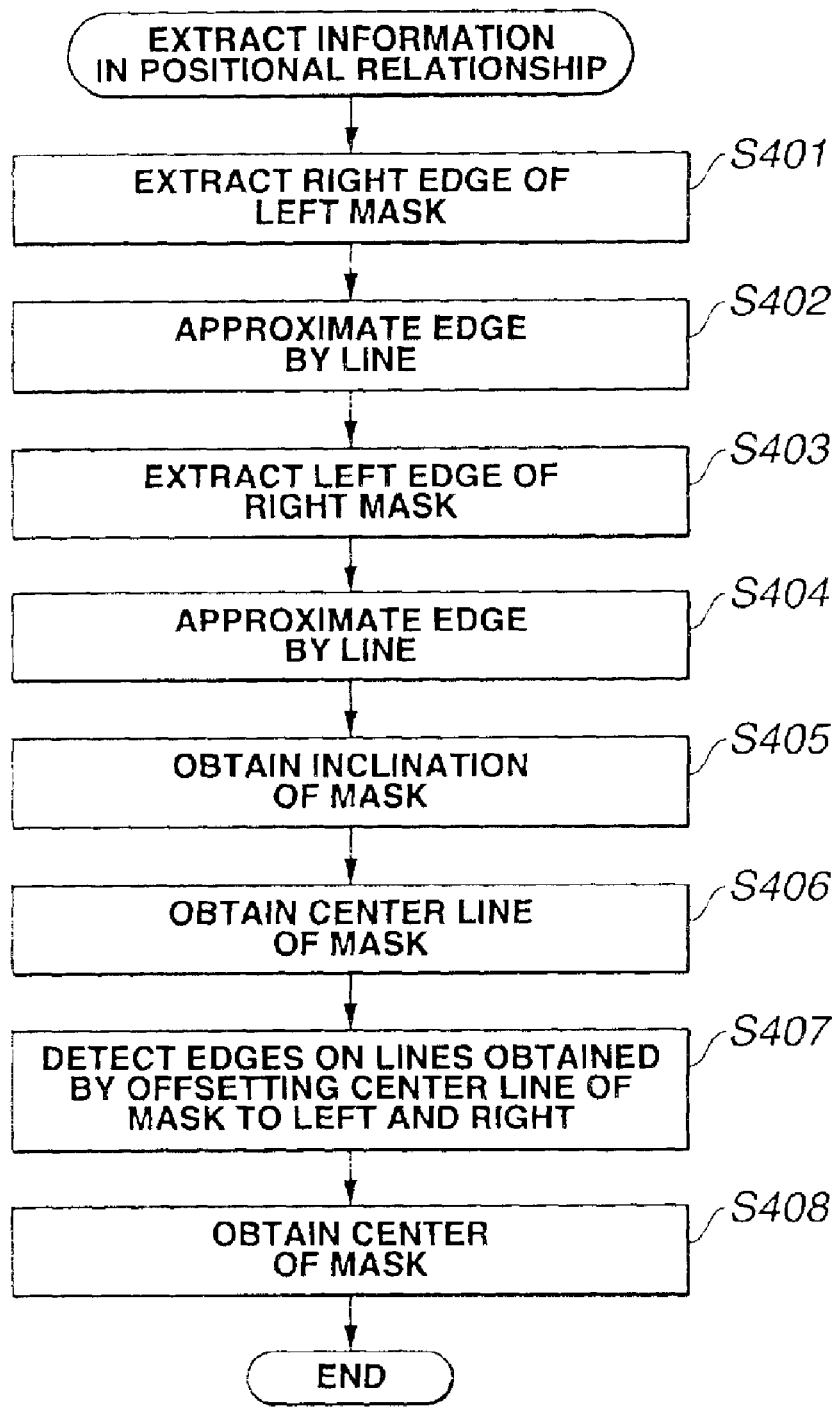
FIG. 18 is a flowchart showing an example of the control operation by a CPU characterized by a fifth embodiment of the present invention.
Figure 19:
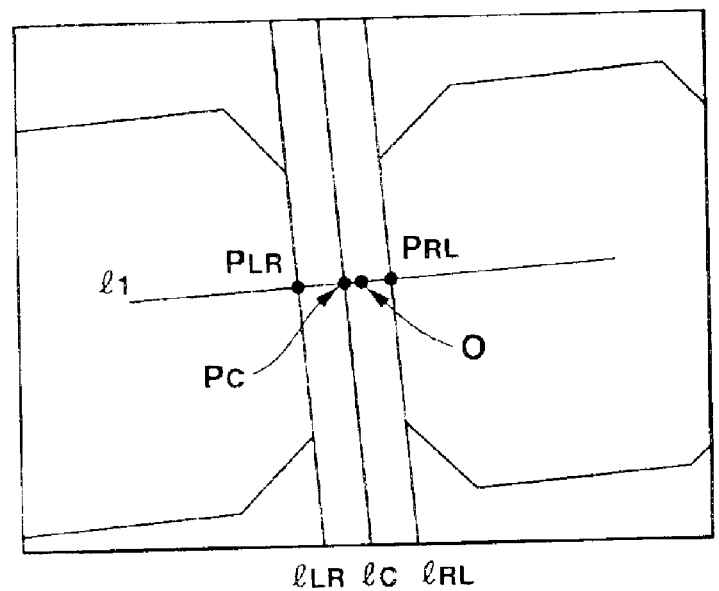
FIG. 19 is a diagram showing images of the shape of a mask of a stereo optical adaptor according to the fifth embodiment.
Figure 20:
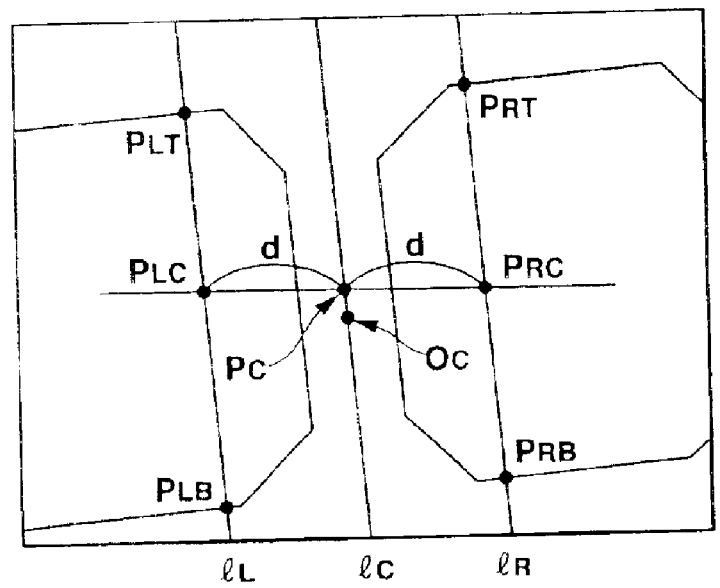
FIG. 20 is a diagram showing images of the shape of the mask for explaining the processing according to the fifth embodiment.

FIGS. 18 to 20 are diagrams for explaining a fifth embodiment of the present invention. FIG. 18 is a flowchart showing an example of the control operation of a CPU in a measuring endoscope apparatus characterized by the fifth embodiment. FIG. 19 is a diagram showing an image of the shape of a mask of the stereo optical adaptor. FIG. 20 is a diagram showing an image of the shape of the mask for explaining processing according to the fifth embodiment. For the fifth embodiment, the same components as those according to the first embodiment are described by using those in FIGS. 1 to 14 therefor.

According to the fifth embodiment, the white image is subjected to processing as shown in FIG. 18 as a part of the calibration.

A right edge of the left mask and a left edge of the right mask are detected (steps S401 and S403). A line passing through the detected edges is approximated by a straight line expressed by the following expression 1 where the x axis denotes the horizontal right direction on the screen, the y axis denotes the vertical descending direction, an inclination is designated by a, and an intercept is designated by b (steps S402 and S404).

$$x = ay + b \quad \text{(expression 1)}$$

Assuming that an inclination of a straight line $l_{LR}$ for approximating the right edge of the left mask is designated by $a_{LR}$ and an inclination of a straight line $l_{RL}$ for approximating the left edge of the right mask is designated by $a_{RL}$, an inclination angle of the mask is obtained by the following expression 2 and an inclination $a_c$ is obtained by the following expression 3 (step S405).

$$\phi = (\tan^{-1} a_{LR} + \tan^{-1} a_{RL})/2 \quad \text{(expression 2)}$$

$$a_c = \tan \phi \quad \text{(expression 3)}$$

A straight line $l_1$ having an inclination $1/a_c$, passing through a screen center O, and intersections $P_{LR}$ and $P_{RL}$ between the two lines $l_{LR}$ and $l_{RL}$ for approximating the obtained edges are obtained. Incidentally, when $a_c=0$, a horizontal line passing through the screen center is expressed by $l_1$ and the intersections $P_{LR}$ and $P_{RL}$ are obtained.

Coordinates of an intermediate point $P_c$ of segment $P_{LR} P_{RL}$ connecting the obtained intersections are obtained. A center line $l_c$ having an inclination $a_c$, passing through the obtained intermediate point $P_c$ is obtained (step S406) (the above-mentioned processing is as shown in FIG. 17).

A straight line $l_L$ obtained by shifting the straight line $l_c$ to the left by a predetermined amount of offset d and a straight line $l_R$ obtained by shifting the straight line $l_c$ to the right by the predetermined amount of offset d are obtained.

A mask edge on the straight line $l_L$ is obtained, and a top point is designated by a point $P_{LT}$ and a bottom point is designated by a point $P_{LB}$. Similarly, a top point $P_{RT}$ and a bottom point $P_{RB}$ are obtained on the straight line $l_R$ (step S407).

An average of coordinates at the four obtained points $P_{LT}$, $P_{LB}$, $P_{RT}$, and $P_{RB}$ is obtained. The obtained point is set by coordinates $(c_x, c_y)$ of a center point $O_c$ of the mask (step S408) (the above processing is as shown in FIG. 18).

The obtained inclination angle φ, the position $c_x$ in the horizontal direction, and the position $c_y$ in the vertical direction are stored as the information on the positional relationship.

The following processing is implemented after reading the recorded image.

An inclination angle φ1, the position $c_x$ in the horizontal direction, and the position $c_y$ in the vertical direction are set as the information on the positional relationship which is read out from the copy of the information on the positional relationship as a part of the image data file.

A straight line having an inclination tan φ1 and a straight line having an inclination 1/tan φ1 which pass through a point of the coordinates $(c_{x1}, c_{y1})$ are overlapped on an image and the resultant is displayed. Incidentally, when φ1=0, a horizontal line and a vertical line which pass through the above-mentioned point are displayed.

An inclination angle φ2, a position $c_{x2}$ in the horizontal direction, and a position $c_{y2}$ in the vertical direction are set as the information on the positional relationship which is read out from the information on the positional relationship of the data on the measurement environment.

A straight line having an inclination tan φ2 and a straight line having an inclination 1/tan φ2 which pass through a point of the coordinates $(c_{x2}, c_{y2})$ are overlapped on an image and the resultant is displayed. Incidentally, when φ2=0, a horizontal line and a vertical line which pass through the above-mentioned point are displayed.

Accordingly, the calculation of the information on the positional relationship can be performed for a shorter time, as compared with that according to the fourth embodiment.

As mentioned above according to the five embodiments, in the present invention, a copy of the information on the positional relationship between the image pick-up device and the optical adaptor, which is generated upon calibration, is stored as first information on the positional relationship in association with the subject image. The comparing and determining means compares the copy of the previous first information on the positional relationship associated with the subject image stored in the past with second information on the positional relationship which is newly generated by executing the calibration again. The comparison result is presented by the notifying means, thus enabling it to easily check whether or not the newly generated information on the positional relationship is valid to the subject image stored in the past. When performing the measuring by using the stored result of the calibration, it is possible to prevent the execution of the calibration from decreasing the precision by the change in positional relationship between the image pick-up device and the optical system of the optical adaptor.

Having described the preferred embodiments of the invention referring to the accompanying drawings, it should be understood that the present invention is not limited to those precise embodiments, but various changes and modifications thereof could be made by one skilled in the art without departing from the spirit or scope of the invention as defined in the appended claims.

What is claimed is:

1. A measuring endoscope apparatus comprising:
    an endoscope insertion portion having an image pick-up unit for observation at a tip thereof;
    a processing unit provided on a proximal end side of said endoscope insertion portion, for receiving an image pick-up signal from said image pick-up unit, processing it, and generating a video signal;
    a display device for receiving and displaying the video signal from said processing unit; and
    a connecting portion for detachably connecting to the tip of said endoscope insertion portion a plurality of types of optical adaptors having an observation optical system for forming an observation image on said image pick-up unit,
    wherein said processing unit comprises:
    an extracting unit for extracting first information on a positional relationship of said optical adaptor by performing image processing of a signal transmitted from said image pick-up unit upon capturing the image of a predetermined subject;
    a storing unit for storing said first information on the positional relationship;
    a comparing and determining unit for comparing the first information on the positional relationship stored in said storing unit with second information on the positional relationship which is extracted again by said extracting unit; and
    a notifying unit for notifying a determination result based on determination information from said comparing and determining unit, said determination result affecting whether or not a re-measuring of data is to take place.

2. The measuring endoscope apparatus according to claim 1, wherein said information on the positional relationship includes data for an inclination angle of the image, upon capturing the image of said subject.

3. The measuring endoscope apparatus according to claim 1, wherein said information on the positional relationship includes data for an inclination angle of the image, a position of the image in the horizontal direction, and a position of the image in the vertical direction, upon capturing the image of said subject.

4. The measuring endoscope apparatus according to claim 3, further comprising:
    positional offset index generating means for generating a positional offset index as an index indicating the difference between said first information on the positional relationship and said second information on the positional relationship, based on said inclination angle, said position in the horizontal direction, and said position in the vertical direction; and
    positional offset index combining means for combining said positional offset index with said video signal.

5. The measuring endoscope apparatus according to claim 1, wherein said processing unit does not start predetermined calculation based on the determination information from said comparing and determining unit.

6. A measuring endoscope apparatus comprising:
    an endoscope insertion portion having an image pick-up unit for observation at a tip thereof;
    a processing unit provided on a base end side of said endoscope insertion portion, for receiving an image pick-up signal from said image pick-up unit, processing it, and generating a video signal;
    a display device for receiving and displaying the video signal from said processing unit; and
    a connecting portion for detachably connecting to the tip of said endoscope insertion portion a plurality of types of optical adaptors having an observation optical system for forming an observation image on said image pick-up unit,
    wherein said processing unit comprises:
    an extracting unit for extracting information on the boundary of a field of view of said optical adaptor by performing the image processing of an image pick-up signal transmitted from said image pick-up unit upon capturing the image of a predetermined subject;
    a storing unit for storing said information on the boundary of the field of view; and
    a combining unit for generating an index of the boundary of the field of view based on said information on the boundary of the field of view stored in said storing unit, and combining said index of the boundary of the field of view with said video signal.

7. The measuring endoscope apparatus according to claim 6, wherein said information on the boundary of the field of view is displayed as a polygon which circumscribes about the shape of the field of view.

8. The measuring endoscope apparatus according to claim 7, wherein said polygon is a quadrilateral.

9. The measuring endoscope apparatus according to claim 8, wherein an index to be reflected within the field of view is provided for said optical adaptor and said predetermined subject image is said index.

10. The measuring endoscope apparatus according to claim 9, wherein said index is a mask for limiting the field of view.

11. The measuring endoscope apparatus according to claim 7, wherein an index to be reflected within the field of view is provided for said optical adaptor and said predetermined subject image is said index.

12. The measuring endoscope apparatus according to claim 11, wherein said index is a mask for limiting the field of view.

13. The measuring endoscope apparatus according to claim 6, wherein an index to be reflected within the field of view is provided for said optical adaptor and said predetermined subject image is said index.

14. The measuring endoscope apparatus according to claim 13, wherein said index is a mask for limiting the field of view.

15. A measuring endoscope apparatus comprising:
    an endoscope insertion portion having an image pick-up unit for observation at a tip thereof;
    a processing unit for receiving an image pick-up signal from said image pick-up unit and generating a video signal;
    a display device for performing the display based on the video signal generated by said processing unit;
    a connecting portion for detachably connecting to the tip of said endoscope insertion portion a plurality of types of optical adaptors having an observation optical system for forming an observation image on said image pick-up unit;

an extracting unit for extracting first information on a positional relationship of said optical adaptor by performing the image processing of a signal transmitted from said image pick-up unit upon capturing the image of a predetermined subject;

a storing unit for storing said first information on the positional relationship;

a comparing and determining unit for comparing the first information on the positional relationship stored in said storing unit with second information on the positional relationship which is extracted again by said extracting unit when said optical adaptor is replaced at the tip of said endoscope insertion portion; and a notifying unit for notifying a determination result based on determination information from said comparing and determining unit, said determination result affecting whether or not a re-measuring of data is to take place.

16. The measuring endoscope apparatus according to claim 15, wherein said information on the positional relationship includes data for an inclination angle of an image, upon image pick-up of said subject.

17. The measuring endoscope apparatus according to claim 15, wherein said information on the positional relationship includes data for an inclination angle of the image, a position of the image in the horizontal direction, and a position of the image in the vertical direction, upon capturing the image of said subject.

18. The measuring endoscope apparatus according to claim 15, wherein said processing unit does not start predetermined calculation based on the determination information from said comparing and determining unit.

* * * * *